US008531911B2

(12) United States Patent
Noguchi

(10) Patent No.: US 8,531,911 B2
(45) Date of Patent: Sep. 10, 2013

(54) ULTRASONIC OBSERVATION APPARATUS, OPERATION METHOD OF THE SAME, AND COMPUTER READABLE RECORDING MEDIUM

(75) Inventor: Hiromasa Noguchi, Mitaka (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 13/469,163

(22) Filed: May 11, 2012

(65) Prior Publication Data

US 2012/0281497 A1 Nov. 8, 2012

Related U.S. Application Data

(63) Continuation of application No. PCT/JP2011/076606, filed on Nov. 11, 2011.

(30) Foreign Application Priority Data

Nov. 11, 2010 (JP) ................................. 2010-253288

(51) Int. Cl.
*G03B 42/06* (2006.01)

(52) U.S. Cl.
USPC ............................................................ 367/11

(58) Field of Classification Search
USPC .................. 367/7, 11, 87; 600/437, 442, 443
See application file for complete search history.

(56) References Cited

U.S. PATENT DOCUMENTS

| | | | |
|---|---|---|---|
| 5,749,364 A | 5/1998 | Sliwa, Jr. et al. | |
| 2003/0179917 A1 | 9/2003 | Faber et al. | |
| 2004/0152983 A1 | 8/2004 | Vince et al. | |
| 2006/0079780 A1 | 4/2006 | Karasawa | |
| 2007/0060817 A1 | 3/2007 | Davies | |
| 2007/0160275 A1 | 7/2007 | Sathyanarayana | |
| 2007/0239007 A1 | 10/2007 | Silverman et al. | |
| 2012/0281497 A1* | 11/2012 | Noguchi | ............................ 367/7 |
| 2013/0096429 A1* | 4/2013 | Noguchi | ........................ 600/438 |

FOREIGN PATENT DOCUMENTS

| | | |
|---|---|---|
| JP | 2004-49925 A | 2/2004 |
| JP | 2005-253827 A | 9/2005 |
| JP | 2007-97671 A | 4/2007 |
| JP | 2007-524431 A | 8/2007 |

(Continued)

OTHER PUBLICATIONS

International Search Report PCT/JP2011/076606 dated Jan. 31, 2012.

Schmitz, G. et al, "Tissue Characterization of the Prostate Using Kohonen-Maps", Ultrasonics Symposium, 1994 Proceedings, Oct. 31, 1994, pp. 1487-1490.

(Continued)

*Primary Examiner* — Daniel Pihulic

(74) *Attorney, Agent, or Firm* — Scully, Scott, Murphy & Presser, P.C.

(57) ABSTRACT

In a feature data space including a first coordinate system that contains at least some of sets of feature data being respectively extracted for known specimens as its coordinate components an ultrasonic observation apparatus calculates coordinate values of the feature data of a specimen in a second coordinate system and assigns display parameters corresponding to the calculated coordinate values, wherein the second coordinate system has a new coordinate axis as one of its coordinate axes, the new coordinate axis is an axis on which sum of distances between adjacent representative points is large, the representative points represent respective groups obtained by classifying the known specimens on the basis of information regarding each known specimen, the distances are obtained when the adjacent representative points, which are adjacent along a predetermined coordinate axis in the first coordinate system, are projected on a predetermined axis.

16 Claims, 14 Drawing Sheets
(2 of 14 Drawing Sheet(s) Filed in Color)

(56) References Cited

FOREIGN PATENT DOCUMENTS

| | | |
|---|---|---|
| JP | 2009-523059 A | 6/2009 |
| JP | 2010-051553 | 3/2010 |
| WO | WO 2005/122906 A1 | 12/2005 |
| WO | WO 2012063978 A1 * | 5/2012 |

OTHER PUBLICATIONS

Supplementary Extended European Search Report dated Jan. 30, 2013 from related application EP 11840642.0-2319.

* cited by examiner

FIG.18
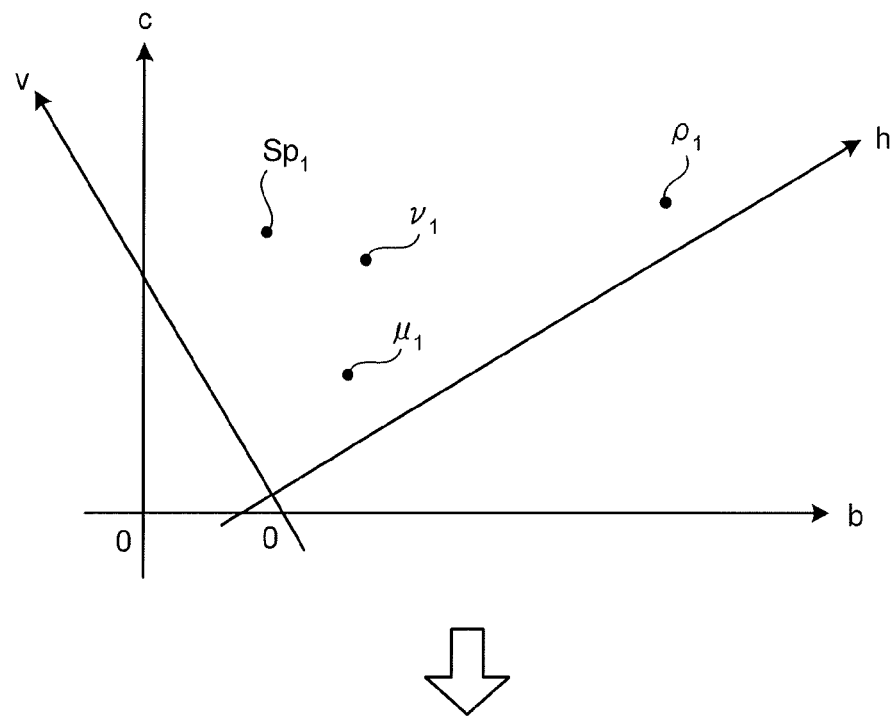
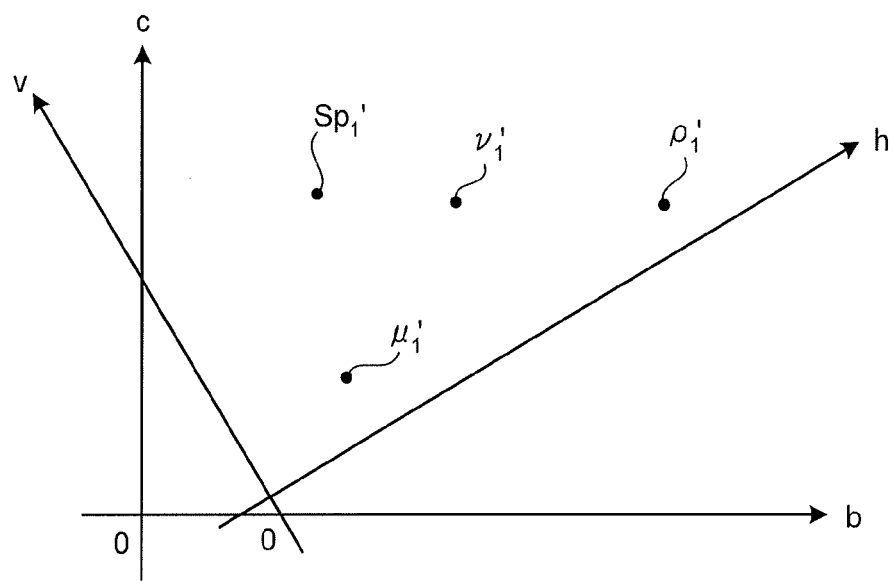

ULTRASONIC OBSERVATION APPARATUS, OPERATION METHOD OF THE SAME, AND COMPUTER READABLE RECORDING MEDIUM

CROSS REFERENCES TO RELATED APPLICATIONS

This application is a continuation of PCT international application Ser. No. PCT/JP2011/076606 filed on Nov. 11, 2011 which designates the United States, incorporated herein by reference, and which claims the benefit of priority from Japanese Patent Applications No. 2010-253288, filed on Nov. 11, 2010, incorporated herein by reference.

BACKGROUND OF THE INVENTION

1. Field of the Invention

The present invention relates to an ultrasonic observation apparatus, an operation method of the ultrasonic observation apparatus, and a computer readable recording medium for enabling observation of tissues of a specimen using ultrasonic sound waves.

2. Description of the Related Art

Typically, in order to perform screening for breast cancer using ultrasonic sound waves, a technology called ultrasonic elastography is known (for example, see WO/2005/122906). The ultrasonic elastography is a technology which makes use of the fact that cancer tissues or tumor tissues inside a body have different hardness depending on the disease progression or depending on the body nature. In this technology, while continually applying external compression to the screening location, the strain amount or the degree of elasticity of the body tissues at the screening location is measured using ultrasonic sound waves, and the measurement result is displayed in the form of cross-sectional images.

SUMMARY OF THE INVENTION

An ultrasonic observation apparatus according to the present invention transmits ultrasonic sound waves to a specimen and receives ultrasonic sound waves reflected from the specimen, the ultrasonic observation apparatus including: a frequency analyzing unit that analyzes frequencies of the received ultrasonic sound waves and calculates a frequency spectrum; a feature data extracting unit that performs approximation with respect to the frequency spectrum calculated by the frequency analyzing unit and extracts a plurality of sets of feature data of the frequency spectrum; and a display parameter assigning unit that, in a feature data space including a first coordinate system that contains at least some of sets of feature data being respectively extracted for known specimens as its coordinate components, calculates coordinate values of the feature data of the specimen in a second coordinate system and assigns display parameters corresponding to the calculated coordinate values, the second coordinate system having a new coordinate axis as one of its coordinate axes, the new coordinate axis being an axis on which sum of distances between adjacent representative points is large, the representative points representing respective groups obtained by classifying the known specimens on the basis of information regarding each known specimen, the distances being obtained when the adjacent representative points, which are adjacent along a predetermined coordinate axis in the first coordinate system, are projected on a predetermined axis.

An operation method of an ultrasonic observation apparatus according to the present invention, which transmits ultrasonic sound waves to a specimen and receives ultrasonic sound waves reflected from the specimen, includes: calculating that includes analyzing frequencies of the received ultrasonic sound waves and calculating a frequency spectrum by a frequency analyzing unit; extracting that includes performing approximation with respect to the frequency spectrum that has been calculated and extracting sets of feature data of the frequency spectrum by a feature data extracting unit; and assigning that includes calculating, in a feature data space including a first coordinate system that contains at least some of sets of feature data being respectively extracted for known specimens as its coordinate components, coordinate values of the feature data of the specimen in a second coordinate system and assigning display parameters corresponding to the calculated coordinate values by a display parameter assigning unit, the second coordinate system having a new coordinate axis as one of its coordinate axes, the new coordinate axis being an axis on which sum of distances between adjacent representative points is large, the representative points representing respective groups obtained by classifying the known specimens on the basis of information regarding each known specimen, the distances being obtained when the adjacent representative points, which are adjacent along a predetermined coordinate axis in the first coordinate system, are projected on a predetermined axis.

A non-transitory computer readable recording medium according to the present invention has an executable program stored thereon, wherein the program instructs a processor to perform: calculating that includes analyzing frequencies of ultrasonic sound waves received from a specimen and calculating a frequency spectrum by a frequency analyzing unit; extracting that includes performing approximation with respect to the frequency spectrum that has been calculated and extracting sets of feature data of the frequency spectrum by a feature data extracting unit; and assigning that includes calculating, in a feature data space including a first coordinate system that contains at least some of sets of feature data being respectively extracted for known specimens as its coordinate components, coordinate values of the feature data of the specimen in a second coordinate system and assigning display parameters corresponding to the calculated coordinate values by a display parameter assigning unit, the second coordinate system having a new coordinate axis as one of its coordinate axes, the new coordinate axis being an axis on which sum of distances between adjacent representative points is large, the representative points representing respective groups obtained by classifying the known specimens on the basis of information regarding each known specimen, the distances being obtained when the adjacent representative points, which are adjacent along a predetermined coordinate axis in the first coordinate system, are projected on a predetermined axis.

The above and other features, advantages and technical and industrial significance of this invention will be better understood by reading the following detailed description of presently preferred embodiments of the invention, when considered in connection with the accompanying drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 18 is a diagram that schematically illustrates an overview of $\gamma$ correction performed by an ultrasonic observation apparatus according to another embodiment of the present invention.

DETAILED DESCRIPTION OF THE PREFERRED EMBODIMENTS

Exemplary illustrative embodiments of the present invention (hereinafter, referred to as "embodiments") are explained below in detail with reference to the accompanying drawings.

First Embodiment

Figure 1:
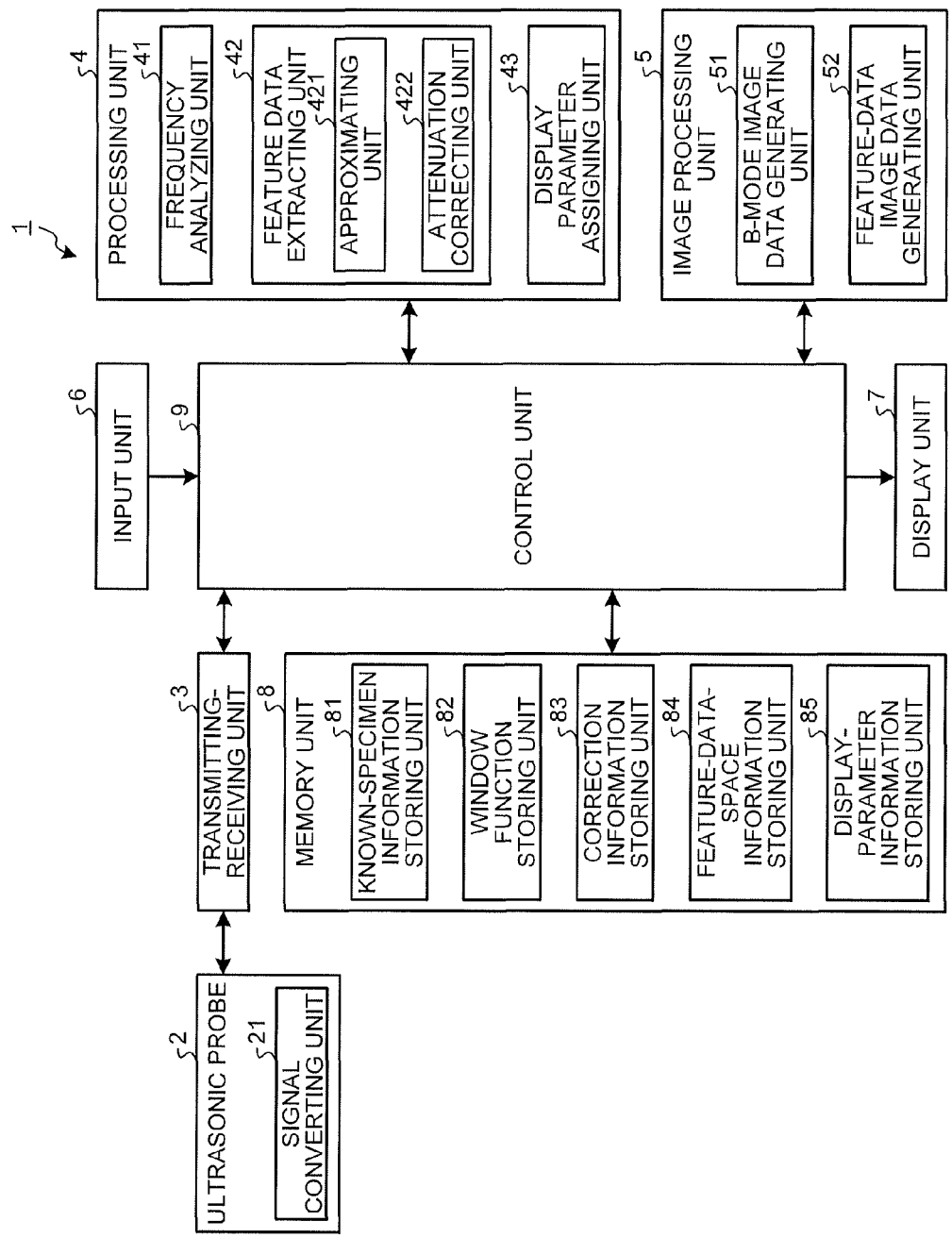
FIG. 1 is block diagram illustrating a configuration of an ultrasonic observation apparatus according to a first embodiment of the present invention.

FIG. 1 is block diagram illustrating a configuration of an ultrasonic observation apparatus according to a first embodiment of the present invention. An ultrasonic observation apparatus 1 illustrated in FIG. 1 is an apparatus for observing a specimen using ultrasonic sound waves.

The ultrasonic observation apparatus 1 includes an ultrasonic probe 2 that outputs an ultrasonic pulse to the outside and receives an ultrasonic echo obtained by reflection on the outside; includes a transmitting-receiving unit 3 that transmits electrical signals to and receives electrical signals from the ultrasonic probe 2; a processing unit 4 that performs predetermined processing on electrical echo signals which are obtained by means of conversion of the ultrasonic echo; an image processing unit 5 that generates image data corresponding to the electrical echo signals which are obtained by means of conversion of the ultrasonic echo; an input unit 6 that is configured with an interface such as a keyboard, a mouse, or a touch-sensitive panel, and that receives input of a variety of information; a display unit 7 that is configured with a liquid crystal display panel or an organic EL display panel, and that is capable of displaying a variety of information including the images generated by the image processing unit 5; a memory unit 8 that is used to store information related to a plurality of known specimens as well as to store known specimens by grouping them into a plurality of groups; and a control unit 9 that controls the operations of the ultrasonic observation apparatus 1.

The ultrasonic probe 2 converts electrical pulse signals that are received from the transmitting-receiving unit 3 into ultrasonic pulse (acoustic pulse signals), and includes a signal converting unit 21 for converting the ultrasonic echo that is obtained by reflection from an outside specimen into electrical echo signals. Meanwhile, the ultrasonic probe 2 can be configured to have an ultrasonic transducer performing scanning in a mechanical manner or can be configured to have a plurality of ultrasonic transducers performing scanning in an electronic manner.

The transmitting-receiving unit 3 is electrically connected to the ultrasonic probe 2. With that, the transmitting-receiving unit 3 transmits pulse signals to the ultrasonic probe 2 and receives echo signals representing reception signals from the ultrasonic probe 2. More particularly, based on a predetermined waveform and a predetermined transmission timing, the transmitting-receiving unit 3 generates pulse signals and transmits those pulse signals to the ultrasonic probe 2.

The transmitting-receiving unit 3 is electrically connected to the ultrasonic probe 2. With that, the transmitting-receiving unit 3 transmits pulse signals to the ultrasonic probe 2 and receives echo signals from the ultrasonic probe 2. More particularly, based on a predetermined waveform and a predetermined transmission timing, the transmitting-receiving unit 3 generates pulse signals and transmits those pulse signals to the ultrasonic probe 2. Moreover, the transmitting-receiving unit 3 performs operations such as amplification and filtering on received echo signals, performs A/D conversion of that echo signals to generate digital RF signals, and outputs those digital RF signals. Meanwhile, when the ultrasonic probe 2 is configured to have a plurality of ultrasonic transducers performing scanning in an electronic manner, the transmitting-receiving unit 3 is configured to include a multichannel circuit for performing beam synthesis corresponding to the ultrasonic transducers.

The processing unit 4 includes a frequency analyzing unit 41 that performs frequency analysis of echo signals by carrying out fast Fourier transformation (FFT) of the digital RF signals that are output by the transmitting-receiving unit 3; includes a feature data extracting unit 42 that extracts feature data of the specimen by performing attenuation correction and approximation with respect to the frequency spectrum (power spectrum) calculated by the frequency analyzing unit 41 so that there is a decrease in the contribution of attenuation, which occurs due to the reception depth and the frequency of ultrasonic sound waves being propagated; and a display parameter assigning unit 43 that assigns display parameters, to be used during image display, to the feature data of the specimen.

The frequency analyzing unit 41 calculates a frequency spectrum with respect to each acoustic ray (line data) by performing fast Fourier transformation of an FFT data group having a predetermined volume of data. Depending on the tissue characterization of the specimen, the frequency spectrum demonstrates a different tendency. That is because of the fact that a frequency spectrum has a correlation with the size, the density, and the acoustic impedance of the specimen that serves as a scatterer which scatters the ultrasonic sound waves.

The feature data extracting unit 42 further includes an approximating unit 421, which performs approximation with respect to the frequency spectrum calculated by the frequency analyzing unit 41 and calculates pre-correction feature data that is the feature data prior to performing attenuation correction; and includes an attenuation correcting unit 422, which extracts feature data by performing attenuation correction with respect to the pre-correction feature data obtained by approximation by the approximating unit 421.

The approximating unit 421 performs linear approximation with respect to the frequency spectrum by means of regression analysis, and extracts feature data that characterizes the approximated linear expression. More particularly, by means of regression analysis, the approximating unit 421 calculates a gradient $a_0$ and an intercept $b_0$ of the linear expression, as well as calculates the intensity at a specific frequency within the frequency band of the frequency spectrum as the pre-correction feature data. In the first embodiment, it is assumed that, at the central frequency $f_{MID}=(f_{LOW}+f_{HIGH})/2$, the approximating unit 421 calculates $c_0=a_0 f_{MID}+b_0$ as the intensity (Mid-band fit). However, that is only one example. Herein, the intensity indicates any one parameter of parameters such as voltage, power, acoustic pressure, and acoustic energy.

Of the three components of feature data, the gradient $a_0$ has a correlation with the size of the scatterer that scatters the ultrasonic sound waves. Generally, it is thought that larger the scatterer, smaller is the value of the gradient. The intercept $b_0$ has a correlation with the size of the scatterer, the difference in acoustic impedances, and the density (consistency) of the scatterer. More particularly, it is thought that larger the scatterer, greater is the value of the intercept $b_0$; greater the acoustic impedance, greater is the value of the intercept $b_0$; and greater the density (concentration) of the scatterer, greater is the value of the intercept $b_0$. The intensity $c_0$ at the central frequency $f_{MID}$ (hereinafter, simply referred to as "intensity $c_0$") is an indirect parameter derived from the gradient $a_0$ and the intercept $b_0$, and represents the spectrum intensity at the center of the valid frequency band. Thus, it is thought that the intensity $c_0$ has a correlation not only with the size of the scatterer, the difference in acoustic impedances, and the density of the scatterer, but also with the luminosity values of B-mode images to a certain extent. Meanwhile, the approximation polynomial calculated by the feature data extracting unit 42 is not limited to a linear expression. Alternatively, it is also possible to use an approximation polynomial of second-order or more.

The following explanation is given for the correction performed by the attenuation correcting unit 422. An attenuation amount A of ultrasonic sound waves can be expressed as:

$$A = 2\alpha z f \quad (1)$$

where, $\alpha$ represents the attenuation rate, z represents the reception depth of ultrasonic sound waves, and f represents the frequency. As is clear from Equation (1), the attenuation amount A is proportional to the frequency f. Regarding a living body, the specific value of the attenuation rate $\alpha$ is in the range of 0 to 1.0 (dB/cm/MHz) and desirably is in the range of 0.3 to 0.7 (dB/cm/MHz), and is determined according to the organ to be observed. For example, if the organ to be observed is pancreas, then the attenuation rate $\alpha$ is set to 0.6 (dB/cm/MHz). Meanwhile, in the first embodiment, the configuration can also be such that the value of the attenuation rate a can be modified by an input from the input unit 6.

The attenuation correcting unit 422 corrects the pre-correction feature data (the gradient $a_0$, the intercept $b_0$, and the intensity $c_0$), which has been calculated by the approximating unit 421, in the following manner:

$$a = a_0 + 2\alpha z \quad (2)$$

$$b = b_0 \quad (3)$$

$$c = c_0 + 2\alpha z f_{MID}(=af_{MID}+b) \quad (4)$$

As is clear from Equations (2) and (4) too, greater the reception depth of ultrasonic sound waves, greater is the amount of correction during the correction performed by the attenuation correcting unit 422. Meanwhile, with reference to Equation (3), the correction related to the intercept indicates identical transformation. That is because of the fact that the intercept is a frequency component corresponding to the frequency 0 (Hz) and does not get attenuated.

In a feature data space having coordinate components in the form of the feature data extracted by the feature data extracting unit 42 and corrected by the attenuation correcting unit 422, the display parameter assigning unit 43 calculates coordinate values of the feature data in a second coordinate system that is set in order to satisfy predetermined conditions for reflecting the tissue characterization of the specimen, and assigns display parameters for determining the display form of images according to the calculated coordinate values. Herein, for example, "tissue characterization" indicates any one of a cancer, an endocrine tumor, a mucinous tumor, a normal tissue, and a vascular channel. If the specimen is pancreas, then chronic pancreatitis and autoimmune pancreatitis are also considered as tissue characterization. The information regarding the feature data space that includes the second coordinate system is stored in the memory unit 8 (described later).

The image processing unit 5 includes a B-mode image data generating unit 51 that generates B-mode image data from echo signals; and includes a feature-data image data generating unit 52 that generates feature-data image data, which contains pixel values determined according to the B-mode image data generated by the B-mode image data generating unit 51 and contains the display parameters assigned by the display parameter assigning unit 43 to the feature data of the specimen.

The B-mode image data generating unit 51 generates B-mode image data by performing signal processing on digital signals using a known technology such as bandpass filtering, logarithmic conversion, gain processing, or contrast processing, and by performing data thinning according to the data step width that is decided in accordance to the display range of images in the display unit 7.

The feature-data image data generating unit 52 generates feature-data image data by making use of the B-mode image data generated by the B-mode image data generating unit 51, by making use of the feature data generated by the feature data extracting unit 42 and then corrected by the attenuation correcting unit 422, and by making use of display parameters assigned to the feature data by the display parameter assigning unit 43.

The memory unit 8 includes a known-specimen information storing unit 81 that is used to store known specimen information including the feature data of known specimens; includes a window function storing unit 82 that is used to store a window function used during frequency analysis performed by the frequency analyzing unit 41; includes a correction information storing unit 83 that is used to store correction information which is referred to by the attenuation correcting unit 422 while performing operations; a feature-data-space information storing unit 84 that is used to store information related to feature data space which is set on the basis of the feature data of known specimens stored in the known-specimen information storing unit 81; and a display-parameter information storing unit 85 that is used to store display parameter information including the relationship between coordinate values and display parameters of new coordinate axes calculated by the display parameter assigning unit 43.

The known-specimen information storing unit 81 is used to store the feature data of frequency spectrums extracted for known specimens and the tissue characterizations of those known specimens in a corresponding manner. Herein, it is assumed that the feature data of a known specimen is extracted by performing an operation similar to that explained in the first embodiment. However, the feature data extracting operation for a known specimen need not be performed in the ultrasonic observation apparatus 1. Meanwhile, with respect to feature data of the frequency spectrum related to a known specimen, the known-specimen information storing unit 81 is also used to store the average and the standard deviation calculated for each group, which is classified on the basis of the information including the tissue characterization of that known specimen, along with all feature data of that known specimen. In the first embodiment, the average and the standard deviation of feature data of a frequency spectrum of ultrasonic reception signals reflect the changes at a cellular level such as enlargement or anomaly of the nucleus in the specimen or reflect the tissue-level changes such as fibrotic growth in the interstitium or substitution of parenchymal tissues with fibers. In consideration of the fact that a unique value is indicated depending on the tissue characterization, the average and the standard deviation of feature data of the frequency spectrum of a known specimen are used to classify tissue characterizations.

The window function storing unit 82 is used to store at least one window function of the window functions such as Hamming, Hanning, and Blackman. The correction information storing unit 83 is used to store the information related to the conversion of Equations (2) to (4).

The feature-data-space information storing unit 84 is used to store, as the information related to the feature data space that is set on the basis of the known specimen information stored in the known-specimen information storing unit 81, the information related to the second coordinate system in which, when a plurality of representative points each representing one of a plurality of groups obtained by classification on the basis of the feature data of a plurality of known specimens is projected on a predetermined axis and when the sum of distances between adjacent representative points along that coordinate axis is considered for comparison, a new coordinate axis having a large sum of distances between adjacent representative points along the direction of that new coordinate axis is considered as one of the coordinate axes.

Figure 2:
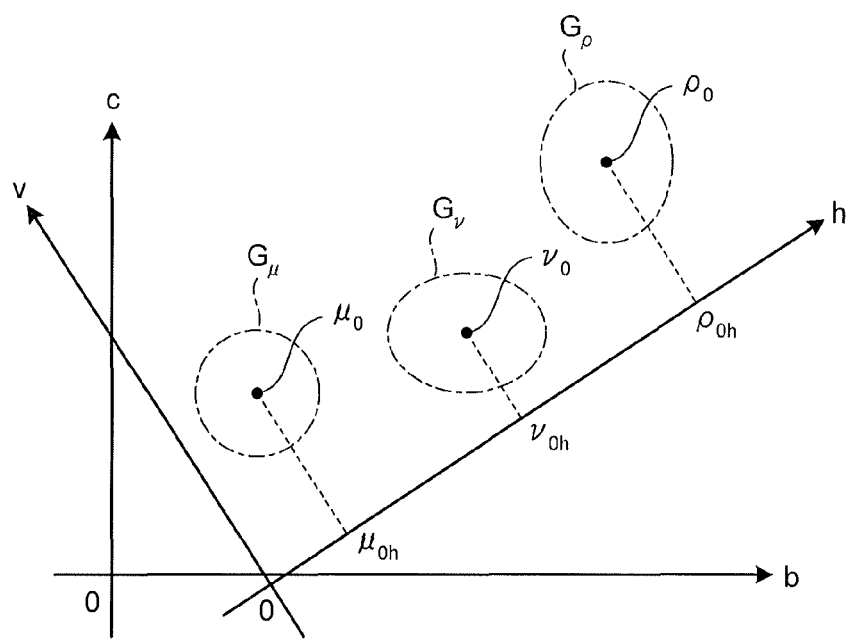
FIG. 2 is a diagram illustrating an overview of feature data space information stored in a feature-data-space information storing unit of the ultrasonic observation apparatus according to the first embodiment of the present invention.

FIG. 2 is a diagram illustrating an overview of the feature data space information stored in the feature-data-space information storing unit 84. In the feature data space illustrated in FIG. 2, the horizontal axis represents the intercept b and the vertical axis represents the intensity c (see Equations (3) and (4)). Moreover, areas $G_\mu$, $G_\nu$, and $G_\rho$ represent groups in which a known specimen stored in the known-specimen information storing unit 81 has tissue characterizations of "$\mu$", "$\nu$", and "$\rho$", respectively. In the case illustrated in FIG. 2, in the feature data space, the three groups $G_\mu$, $G_\nu$, and $G_\rho$ are present in mutually exclusive areas. Thus, in the first embodiment, by classifying the groups with the feature data of the frequency spectrums, which is obtained during frequency analysis, serving as the index; it becomes possible to make distinction between mutually different groups. Particularly, in the first embodiment, attenuation correction is performed with respect to ultrasonic echo signals. Therefore, as compared to the case of not performing attenuation correction, each group in the feature data space can be obtained in a more distinctly separated state. Meanwhile, if the b-axis component and the c-axis component in the feature data space differ in scale by a large extent, it is desirable to appropriately perform weighting so that each distance contributes in a substantial equal manner.

In FIG. 2, apart from a first coordinate system (b, c); a second coordinate system (h, v) is also illustrated. Herein, for points $\mu_0$, $\nu_0$, and $\rho_0$ (hereinafter, referred to as "representative points"), the average intercept b and the average intensity c of the frequency spectrums of an FFT data group included in the groups $G_\mu$, $G_\nu$, and $G_\rho$, respectively, serve as the coordinates in the feature data space. When those representative points $\mu_0$, $\nu_0$, and $\rho_0$ are projected; the coordinate axis h indicates the axis (new coordinate axis) having the maximum sum of distances between adjacent representative points along the direction of projection. Thus, when the components in the h-axis direction of the representative points $\mu_0$, $\nu_0$, and $\rho_0$ are $\mu_{0h}$, $\nu_{0h}$, and $\rho_{0h}$, respectively; the h-axis is defined as the axis along the direction in which $|\mu_0-\nu_0|+|\nu_0-\rho_0|$ is the largest. Meanwhile, the v axis (second new coordinate axis) that is orthogonal to the h axis need not be set.

The display-parameter information storing unit 85 is used to store the coordinate values of the abovementioned new coordinate axis and the display parameters, which determine the display form of images, in a corresponding manner in the feature data space stored in the feature-data-space information storing unit 84. In the first embodiment, for example, the coordinate values in the h axis are stored in a corresponding manner to hues, which serve as one of the three attributes of light. Moreover, in the first embodiment, the coordinate values in the v axis are stored in a corresponding manner to the luminosity values, which serve as one of the three attributes of light and which are fixed independent of hues. Meanwhile, the display parameters are not limited to the abovementioned attributes of light. For example, as the display parameters, it is possible to use the color intensity values, which serve as the remaining attribute of the three attributes of light, or to use variables (such as variables of the RGB color system or a complementary color system) that constitute a color space in general. Alternatively, patterns can also be considered as the display parameters. In the case of using patterns as the display parameters, the setting can be such that the pattern changes for each band of coordinate values.

Meanwhile, the memory unit 8 is put into practice with a ROM, which is used to store in advance operating programs of the ultrasonic observation apparatus 1 according to the first embodiment and to store programs for running a predetermined OS; and with a RAM, which is used to store operating parameters and data of each operation.

In the ultrasonic observation apparatus 1 having the above-mentioned functional configuration, the constituent elements other than the ultrasonic probe 2 are put into practice with a computer that includes a CPU for performing processing and control. The CPU in the ultrasonic observation apparatus 1 reads, from the memory unit 8, the information and various programs including the operating programs of the ultrasonic observation apparatus 1; and performs processing related to the operation method of the ultrasonic observation apparatus 1 according to the first embodiment.

The operating programs of the ultrasonic observation apparatus 1 can also be recorded in a computer readable recording medium such as a hard disk, a flash memory, a CD-ROM, a DVD-ROM, or a flexible disk for the purpose of distribution.

Figure 3:
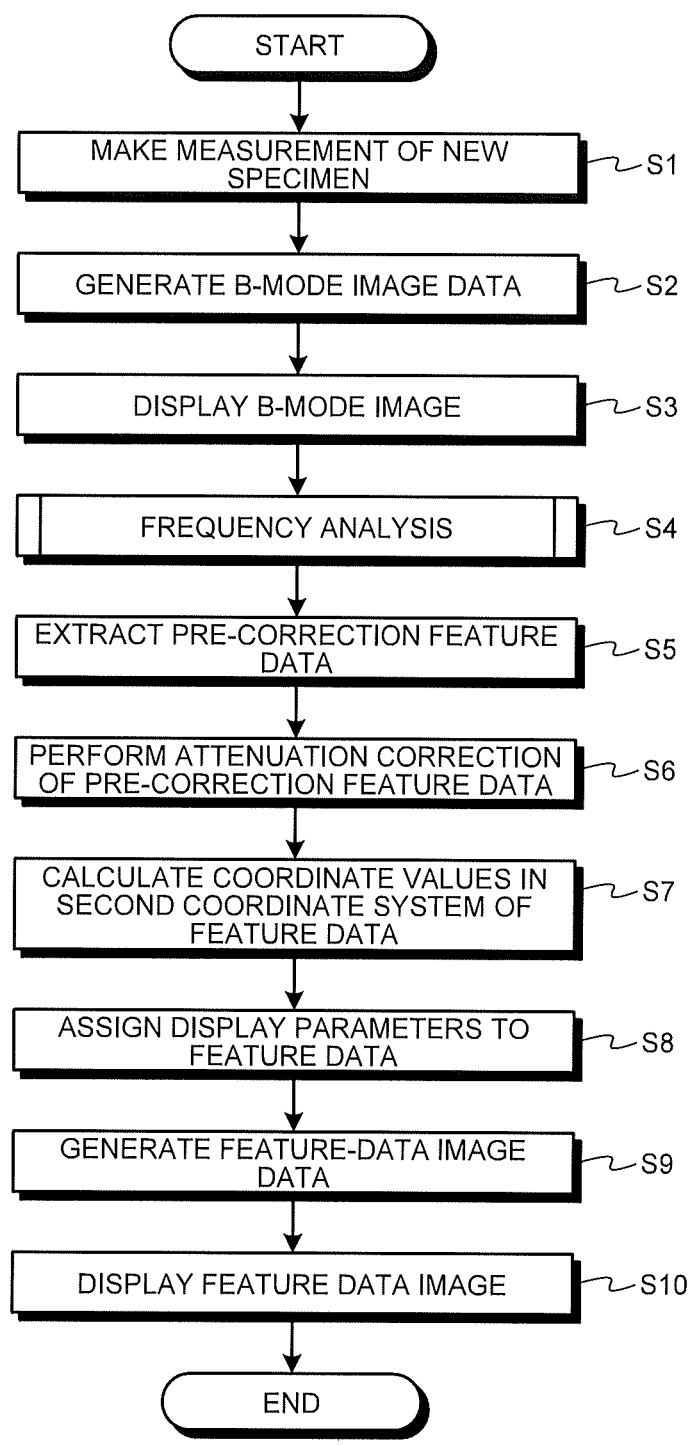
FIG. 3 is a flowchart illustrating an overview of the operations performed by the ultrasonic observation apparatus according to the first embodiment of the present invention.

FIG. 3 is a flowchart illustrating an overview of the operations performed by the ultrasonic observation apparatus 1 having the configuration explained above. With reference to FIG. 3, firstly, the ultrasonic observation apparatus 1 makes a measurement of a new specimen using the ultrasonic probe 2 (Step S1).

Then, the B-mode image data generating unit 51 generates B-mode image data using echo signals for B-mode images output by the transmitting-receiving unit 3 (Step S2).

Figure 4:
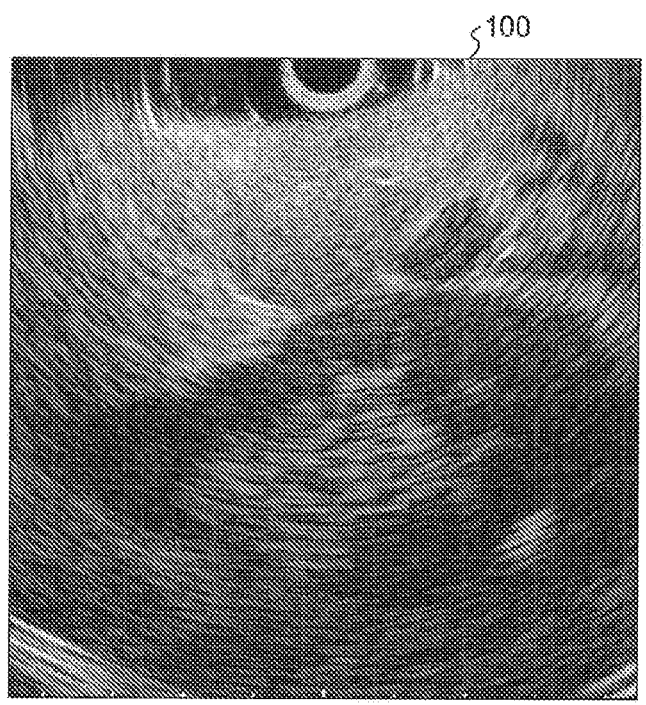
FIG. 4 is a diagram illustrating an example of a B-mode image displayed by a display unit of the ultrasonic observation apparatus according to the first embodiment of the present invention.

Subsequently, the control unit 9 performs control so that the display unit 7 displays the B-mode images corresponding to the B-mode image data generated by the B-mode image data generating unit 51 (Step S3). FIG. 4 is a diagram illustrating an example of a B-mode image displayed by the display unit 7. A B-mode image 100 illustrated in FIG. 4 is a grayscale image in which variables R (red), G (green), and B (blue), which are variables when the RGB color system is adopted as the color space, have identical values.

Figure 5:
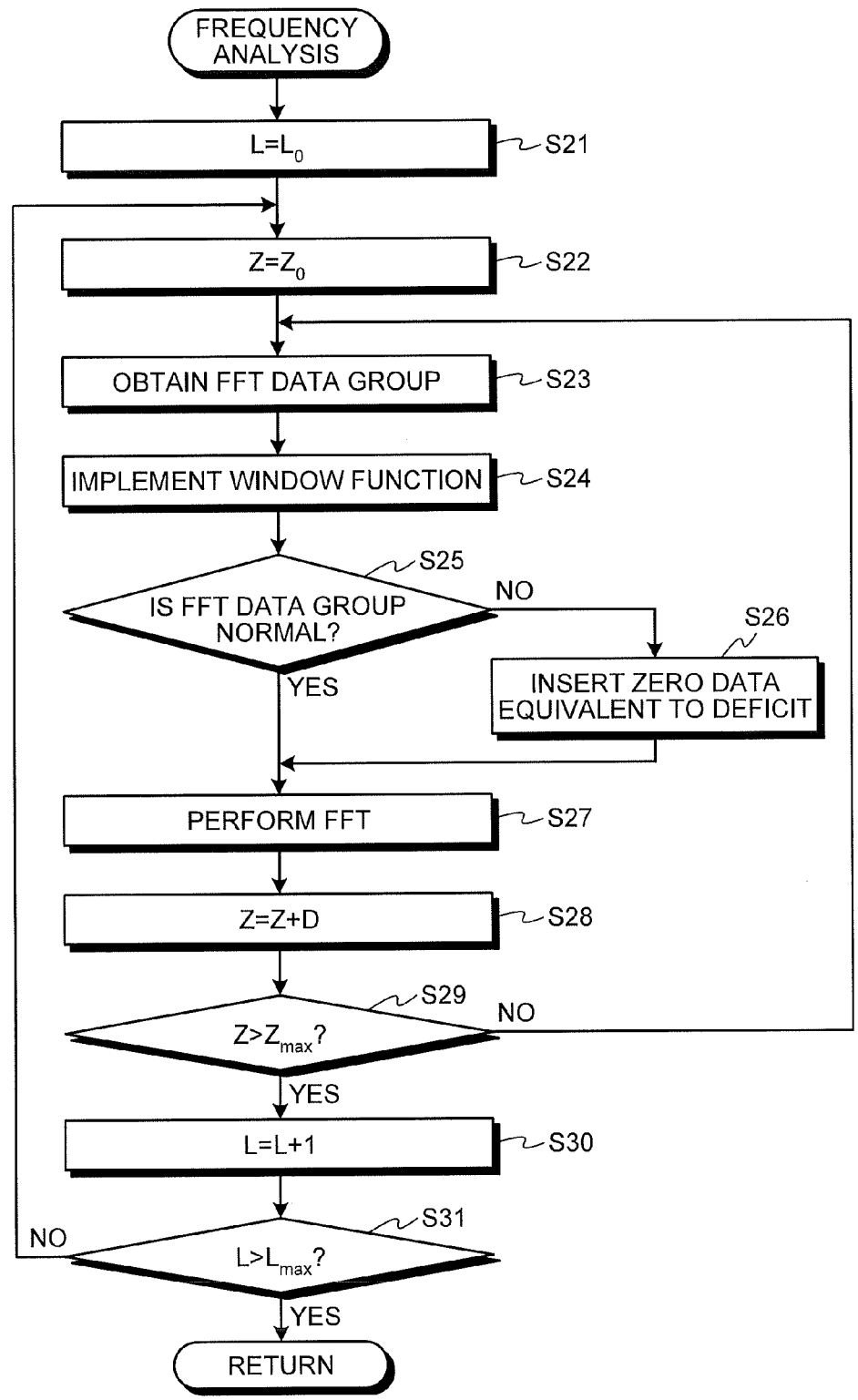
FIG. 5 is a flowchart illustrating an overview of the operations performed by a frequency analyzing unit of the ultrasonic observation apparatus according to the first embodiment of the present invention.

Then, the frequency analyzing unit 41 performs frequency analysis by means of FFT and calculates a frequency spectrum (Step S4). Herein, the operation performed by the frequency analyzing unit 41 at Step S4 is explained in detail with reference to a flowchart illustrated in FIG. 5. Firstly, the frequency analyzing unit 41 sets an acoustic ray number L of the acoustic ray to be initially analyzed to an initial value $L_0$ (Step S21). The initial value $L_0$ can be assigned, for example, to the acoustic ray received at the start by the transmitting-receiving unit 3 or to the acoustic ray corresponding to the border position on any one of the left and right sides of the area of concern set via the input unit 6.

Figure 6:
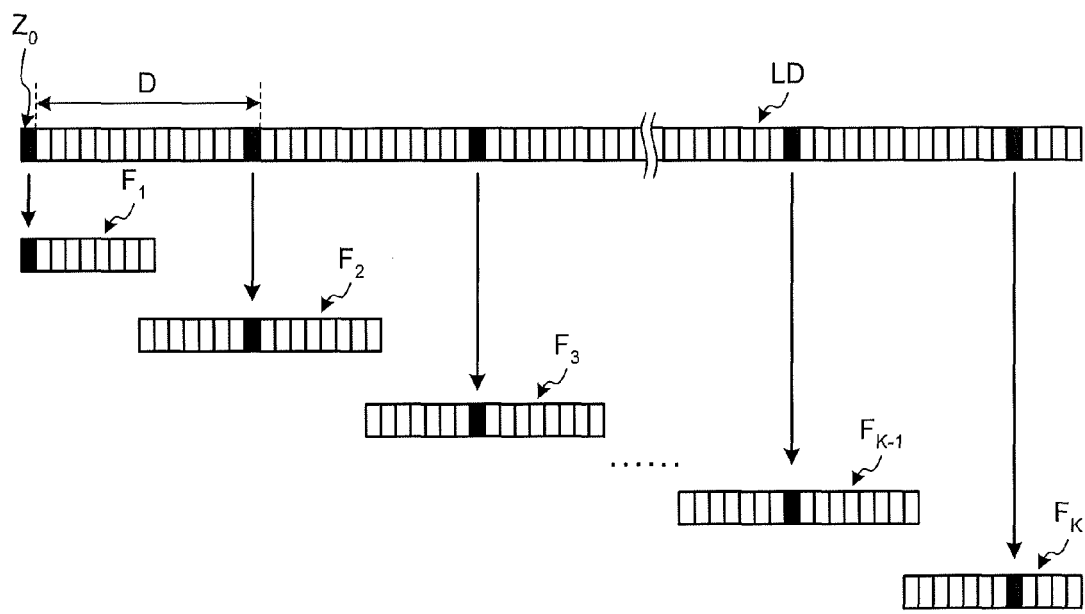
FIG. 6 is a diagram that schematically illustrates data arrangement of a single acoustic ray.

Then, the frequency analyzing unit 41 calculates the frequency spectrum of all data positions set on a single acoustic ray. Regarding that, firstly, the frequency analyzing unit 41 sets an initial value $Z_0$ of a data position Z (equivalent to reception depth) that is representative of a sequence of data groups (FFT data groups) obtained for the purpose of FFT (Step S22). FIG. 6 is a diagram that schematically illustrates data arrangement of a single acoustic ray. In an acoustic ray LD illustrated in FIG. 6, a white rectangle or a black rectangle represents a single set of data. The acoustic ray LD is discretized by time intervals corresponding to the sampling frequency (such as 50 MHz) used during A/D conversion performed by the transmitting-receiving unit 3. In FIG. 6, it is illustrated that the first set of data on the acoustic ray LD is set as the initial value $Z_0$ of the data position Z. Meanwhile, FIG. 6 is only an example, and the position of the initial value $Z_0$ can be set in an arbitrary manner. For example, the data position Z corresponding to the position at the top edge of the area of concern can be set as the initial value $Z_0$.

Then, the frequency analyzing unit 41 obtains the FFT data group at the data position Z (Step S23) and implements the window function, which is stored in the window function storing unit 82, to the FFT data group that has been obtained (Step S24). By implementing the window function to the FFT data group, it becomes possible to avoid discontinuity at the borders in the FFT data group. As a result, artifacts can be prevented from occurring.

Subsequently, the frequency analyzing unit 41 determines whether or not the FFT data group at the data position Z is a normal data group (Step S25). Herein, it is necessary that the number of sets of data in a FFT data group is in power-of-two. In the following explanation, it is assumed that the number of sets of data in the FFT data group is $2^n$ (where n is a positive integer). When a FFT data group is normal, it means that the data position Z is the $2^{n-1}$-th position from the front of the FFT data group. In other words, when a FFT data group is normal, it means that there are $2^{n-1}-1$ (=N) number of sets of data prior to the data position Z, and there are $2^{n-1}$ (=M) number of sets of data subsequent to the data position Z. In the example illustrated in FIG. 6, FFT data groups $F_2$, $F_3$, and $F_{K-1}$ are normal data groups; while FFT data groups $F_1$ and $F_K$ are abnormal data groups. However, in FIG. 6, it is assumed that n=4 (N=7, M=8).

If the determination result of Step S25 indicates that the FFT data group at the data position Z is normal (Yes at Step S25), then the system control proceeds to Step S27 (described later).

If the determination result of Step S25 indicates that the FFT data group at the data position Z is not normal (No at Step S25), then the frequency analyzing unit 41 inserts zero data equivalent to the deficit and generates a normal FFT data group (Step S26). To the FFT data group that is determined to be not normal at Step S25, the function window is implemented prior to the addition of zero data. Hence, even if zero data is inserted, discontinuity in data does not occur. Once the operation at Step S26 is completed, the system control proceeds to Step S27.

Figure 7:
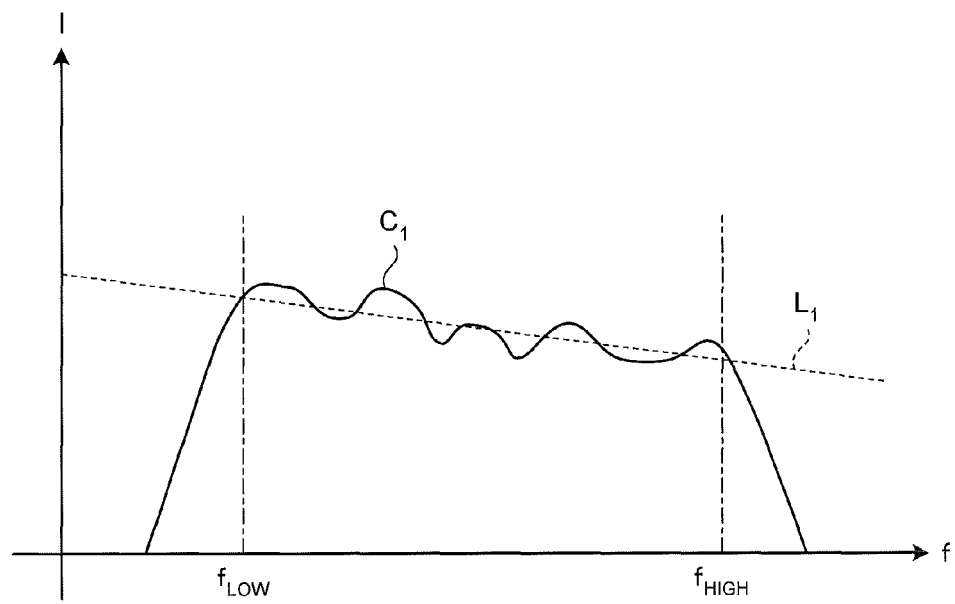
FIG. 7 is a diagram illustrating an example (first example) of the frequency spectrum calculated by the frequency analyzing unit of the ultrasonic observation apparatus according to the first embodiment of the present invention.
Figure 8:
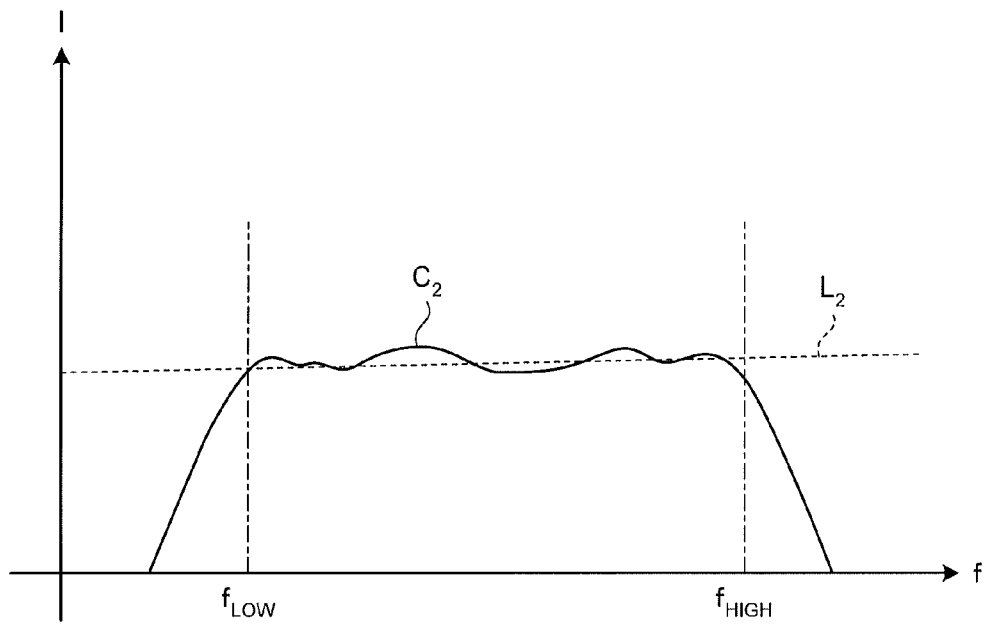
FIG. 8 is a diagram illustrating an example (second example) of the frequency spectrum calculated by the frequency analyzing unit of the ultrasonic observation apparatus according to the first embodiment of the present invention.

At Step S27, the frequency analyzing unit 41 performs FFT using the FFT data groups and obtains the frequency spectrum (Step S27). FIG. 7 and FIG. 8 are diagrams illustrating examples of the frequency spectrum calculated by the frequency analyzing unit 41. In FIG. 7 and FIG. 8, the horizontal axis f represents the frequency and the vertical axis I represents the intensity. In frequency spectrum curves $C_1$ and $C_2$ illustrated in FIG. 7 and FIG. 8, respectively; a lower limit frequency $f_{LOW}$ and a high limit frequency $f_{HIGH}$ of the frequency spectrum are parameters determined on the basis of the frequency band of the ultrasonic probe 2 and the frequency band of the pulse signals transmitted by the transmitting-receiving unit 3. For example, $f_{LOW}$ is equal to 3 MHz and $f_{HIGH}$ is equal to 10 MHz. Meanwhile, regarding a straight line $L_1$ illustrated in FIG. 7 and a straight line $L_2$ illustrated in FIG. 8, the explanation is given later while explaining the feature data extracting operation. In the first embodiment, curve lines and straight lines are formed of sets of discreet points. The same is the case in other embodiments described later.

Subsequently, the frequency analyzing unit 41 adds a predetermined data step width D to the data position Z, and calculates the data position Z at the FFT data group to be analyzed next (Step S28). Herein, it is desirable that the data step width D is matched with the data step width used at the time when the B-mode image data generating unit 51 generates B-mode image data. However, when the object is to reduce the amount of operations in the frequency analyzing unit 41, it is also possible to set the data step width D to a larger value than the data step width used by the B-mode image data generating unit 51. In FIG. 6, it is illustrated that D=15.

Subsequently, the frequency analyzing unit 41 determines whether or not the data position Z is greater than a final data position $Z_{max}$ (Step S29). Herein, the final data position $Z_{max}$ can be set to the data length of the acoustic ray LD or to the data position corresponding to the lower edge of the area of concern. If the determination result indicates that the data position Z is greater than the final data position $Z_{max}$ (Yes at Step S29), then the frequency analyzing unit 41 increments the acoustic ray number L by 1 (Step S30). On the other hand, if the determination result indicates that the data position Z is equal to or smaller than the final data position $Z_{max}$ (No at Step S29), then the system control returns to Step S23. In this way, with respect to a single acoustic ray LD, the frequency analyzing unit 41 performs FFT for $[\{(Z_{max}-Z_0)/D\}+1]$ (=K) number of FFT data groups. Herein, [X] represents the largest integer not exceeding X.

If the acoustic number L that has been incremented at Step S30 is greater than a final acoustic number $L_{max}$ (Yes at Step S31), then the system control returns to the main routine illustrated in FIG. 3. On the other hand, if the acoustic number L that has been incremented at Step S30 is equal to or smaller than the final acoustic number L. (No at Step S31), then the system control returns to Step S22.

In this way, the frequency analyzing unit 41 performs FFT for K number of times with respect to each of $(L_{max}-L_0+1)$ number of acoustic rays. For example, the final acoustic ray number $L_{max}$ can be assigned to the final acoustic ray received by the transmitting-receiving unit 3 or to the acoustic ray corresponding to the border position on any one of the left and right sides of the area of concern. In the following explanation, the total number of times for which the frequency analyzing unit 41 performs FFT with respect to all acoustic rays is $(L_{max}-L_0+1)\times K$ and is referred to as "P".

Subsequent to the frequency analyzing operation performed at Step S4 as described above, the approximating unit 421 performs, as an approximation operation, regression analysis of the P number of frequency spectrums calculated by the frequency analyzing unit 41 and extracts the pre-correction feature data (Step S5). More particularly, the approximating unit 421 performs regression analysis and calculates the linear expression for approximation of the frequency spectrums in the frequency band of $f_{LOW} < f < f_{HIGH}$; and then calculates the gradient $a_0$, the intercept $b_0$, and the intensity $c_0$, which characterize the linear expression, as the pre-correction feature data. The straight line $L_1$ illustrated in FIG. 7 and the straight line $L_2$ illustrated in FIG. 8 are regression lines obtained by performing regression analysis of the frequency spectrum curve $C_1$ and the frequency spectrum curve $C_2$, respectively, at Step S5.

Figure 9:
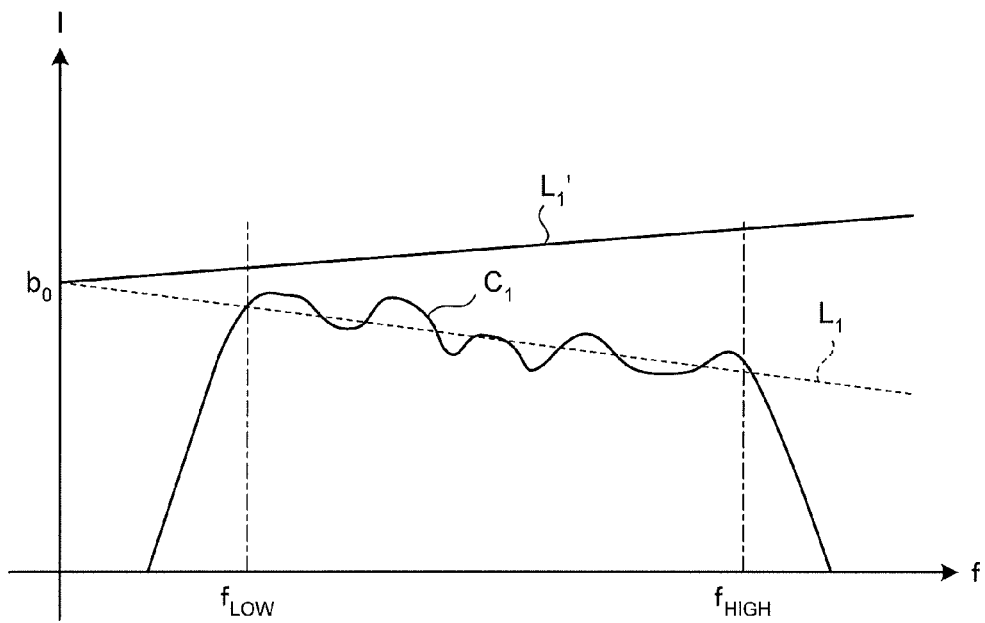
FIG. 9 is a diagram illustrating a new straight line that is determined from the feature data obtained upon performing attenuation correction of the feature data related to a straight line illustrated in FIG. 7.

Then, the attenuation correcting unit 422 performs attenuation correction of the pre-correction feature data extracted by the approximating unit 421 (Step S6). For example, when the data sampling frequency is 50 MHz, the time interval for data sampling is 20 (nsec). If the velocity of sound is assumed to be 1530 (m/sec), then the spacing among data sampling is equal to 1530 (m/sex)×20 (nsec)/2=0.0153 (mm). If "k" is assumed to be the number of data steps from the first set of data of the acoustic ray LD up to the data position of the FFT data group to be processed, then the data position Z thereof is equal to 0.0153 k (mm). The attenuation correcting unit 422 substitutes the value of the data position Z, which is obtained in the manner described above, in the reception depth z specified in Equations (2) to (4) mentioned above, and calculates the gradient a, the intercept b, and the intensity c. FIG. 9 is a diagram illustrating a straight line that is determined from the feature data obtained upon performing attenuation correction of the feature data related to the straight line $L_1$ illustrated in FIG. 7. A straight line $L_1'$ illustrated in FIG. 9 can be expressed as:

$$I=af+b=(a_0+2\alpha Z)f+b_0 \quad (5)$$

As is clear from Equation (5), as compared to the straight line $L_1$, the straight line $L_1'$ has a greater gradient with the same intercept value.

Figure 10:
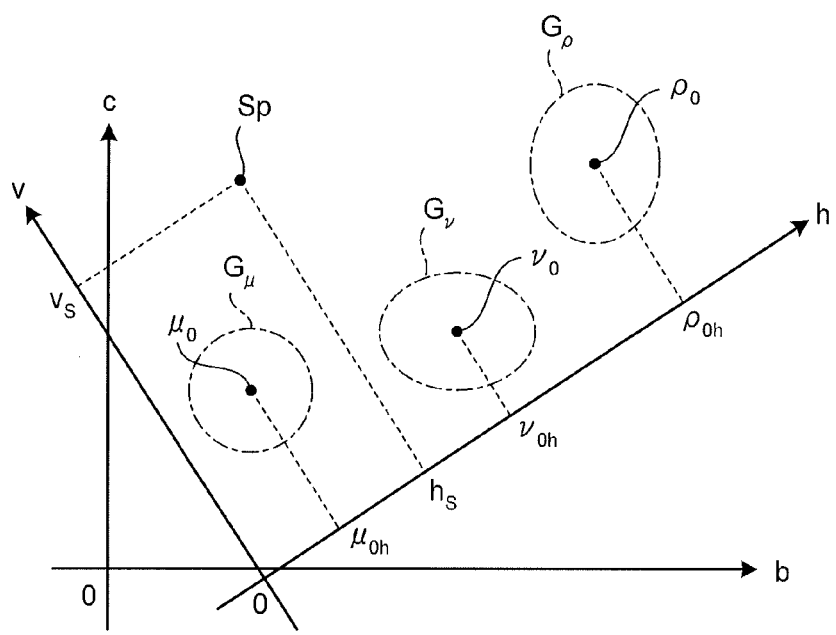
FIG. 10 is a diagram illustrating an overview of a coordinate value calculating operation performed by a display parameter assigning unit of the ultrasonic observation apparatus according to the first embodiment of the present invention.

Subsequently, based on the feature data extracted by the feature data extracting unit 42 and corrected by the attenuation correcting unit 422 as well as based on the known specimen information stored in the known-specimen information storing unit 81 and the feature data space information stored in the feature-data-space information storing unit 84, the display parameter assigning unit 43 calculates the coordinate values in the second coordinate system of the feature data of the specimen (Step S7). FIG. 10 is a diagram illustrating an overview of a coordinate value calculating operation performed in this case. More particularly, in FIG. 10, it is illustrated that, in the feature data space illustrated in FIG. 2, regarding a point Sp representing the feature data extracted for the specimen to be observed (herein, referred to as "specimen point Sp"), coordinate values $(h_s, v_s)$ in the second coordinate system of the specimen point Sp is calculated.

Then, the display parameter assigning unit 43 assigns display parameters corresponding to the coordinate values of the second coordinate system calculated at Step S7 (Step S8). At that time, the display parameter assigning unit 43 assigns the display parameters by referring to the information stored in the display-parameter information storing unit 85.

Once the operation at Step S8 is completed, the feature-data image data generating unit 52 generates feature-data image data using the B-mode image data, which is generated by the B-mode image data generating unit 51, and the display parameters, which are assigned on a pixel-by-pixel basis by the display parameter assigning unit 43 (Step S9).

Figure 11:
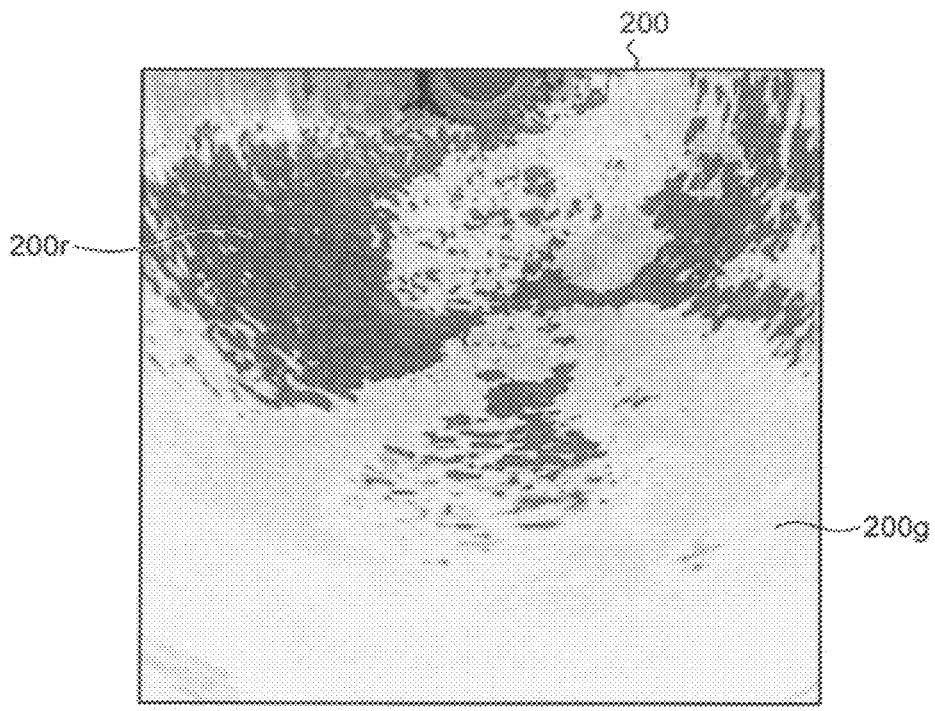
FIG. 11 is a diagram illustrating an example of a feature data image displayed by the display unit of the ultrasonic observation apparatus according to the first embodiment of the present invention.
Figure 12:
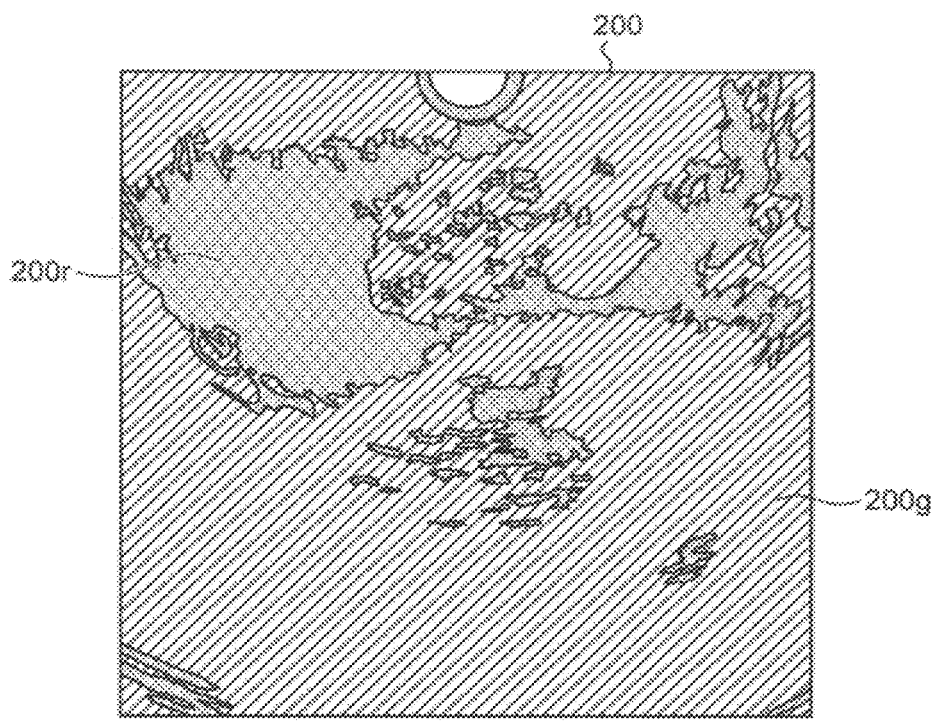
FIG. 12 is a diagram that schematically illustrates a black-and-white image of the image is illustrated in FIG. 11.

Subsequently, the display unit 7 displays a feature data image generated by the feature-data image data generating unit 52 (Step S10). FIG. 11 is a diagram illustrating an example of a feature data image displayed by the display unit 7. FIG. 12 is a diagram that schematically illustrates a black-and-white image of the image is illustrated in FIG. 11. As compared to the B-mode image 100, a feature data image 200 illustrated in FIG. 11 and FIG. 12 is colorized in such a manner that there is a clear difference in colors according to the groups. The feature data image 200 can be broadly divided into a greenish area 200g and a reddish area 200r, with the boundary portion between those two portions displayed in a yellowish color (not illustrated in FIG. 12). As illustrated in FIG. 11, it is not the case that each area is made of only a single color. For example, the greenish area 200g is an area including pixels having colors close to the green color. Similarly, the reddish area 200r is an area including pixels having colors close to the red color. Thus, the observer who observes the feature data image 200 can clearly recognize the differences in groups, that is, clearly recognizes the differences in tissue characterizations.

Figure 13:
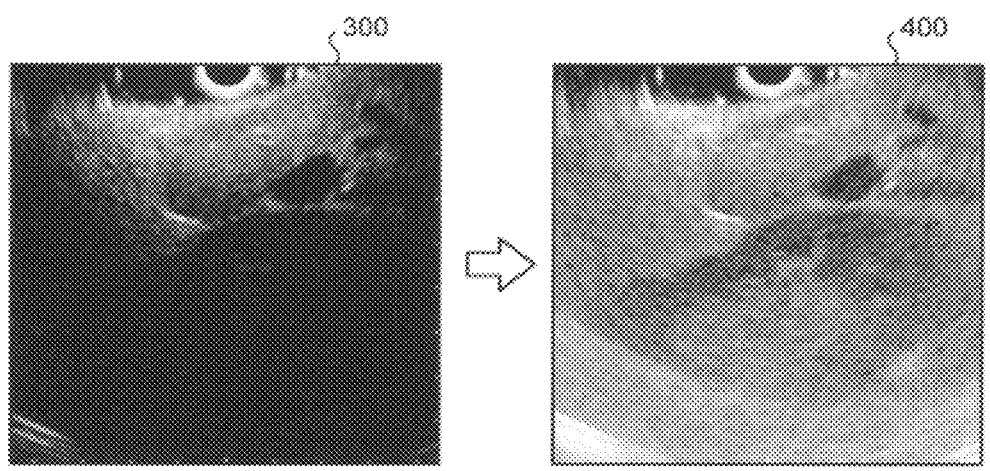
FIG. 13 is a diagram explaining the effect of attenuation correction performed in the first embodiment of the present invention.

FIG. 13 is a diagram explaining the effect of attenuation correction performed in the first embodiment. An image 300 illustrated in FIG. 13 is a feature data image not subjected to attenuation correction. In such a case, in contrast to a B-mode image generated by the B-mode image data generating unit 51, the feature data image is a greyscale image in which the intercept b is equally assigned among R (red), G (green), and B (blue). In the feature data image 300, in the area having a large reception depth (the lower area in FIG. 13), the signal intensity decreases due to the effect of attenuation, thereby making the image darker. In contrast, regarding a feature data image 400 for which attenuation correction is performed using the same B-mode image, it can be seen that the image has got a uniform brightness throughout the screen.

As described above, according to the first embodiment of the present invention, in a feature data space including a first coordinate system that has at least some of a plurality of sets of feature data, each of which being extracted with respect to one of a plurality of known specimens, as coordinate components; when a plurality of representative points each representing one of a plurality of groups obtained by classification on the basis of the information regarding each of a plurality of known specimens is projected on a predetermined axis, a new coordinate axis having a large sum of distances between adjacent representative points along a predetermined direction in the first coordinate system is considered as one of the coordinate axes of a second coordinate system, and the coordinate values of the feature data of a specimen in that second coordinate system are calculated and display parameters corresponding to the calculated coordinate values are assigned. Hence, it becomes possible to make clear distinction between different groups. As a result, the specimen can be observed with more accuracy as well as the observation result can be enhanced in terms of reliability.

Moreover, according to the first embodiment, since the coordinate values of the feature data of the specimen in the second coordinate system are calculated, since display parameters corresponding to the coordinate values are assigned, and since feature-data image data having pixel values determined according to the assigned display parameters is generated and displayed; it becomes possible for the user to clearly recognize the differences in the groups in an image.

Furthermore, according to the first embodiment, since attenuation correction is performed on the pre-correction feature data that is extracted from a frequency spectrum, it becomes possible to eliminate the effect of attenuation that occurs during the propagation of ultrasonic sound waves. That makes it possible to perform observation with a higher degree of accuracy.

Meanwhile, in the first embodiment, after the attenuation correcting unit 422 performs attenuation correction of the feature data at Step S6 illustrated in FIG. 3; it is also possible to determine, before proceeding to Step S7, the tissue characterization of the specimen on the basis of the feature data. However, in this case, it is necessary that the feature data of a known specimen and the tissue characterization are stored in a corresponding manner in the known-specimen information storing unit 81.

Explained below is a specific operation performed by the ultrasonic observation apparatus 1 to determine the tissue characterization. The processing unit 4 of the ultrasonic observation apparatus 1 calculates the distances from the specimen point Sp in the feature data space to the representative points $\mu_0$, $\nu_0$, and $\rho_0$ of the groups; and determines that the specimen point Sp belongs to the group having the smallest distance.

In case the distances between the coordinate values and representative points are extremely large; then, even if the smallest value is obtained, the result of determining the tissue characterization is low in terms of reliability. In that regard, when the distances between the specimen point Sp and the representative points are greater than a predetermined threshold value, the ultrasonic observation apparatus 1 can be configured to output an error signal. Moreover, when there are two or more of that smallest value of distances between the specimen point Sp and the representative points, the ultrasonic observation apparatus 1 can be configured to select all tissue characterizations corresponding to the smallest values or to select only one tissue characterization according to predetermined rules. In the latter case, for example, a method can be implemented in which the tissue of a high-grade cancer is set to have a high priority. Meanwhile, alternatively, when there are two or more of that smallest value of distances between the specimen point Sp and the representative points, the ultrasonic observation apparatus 1 can be configured to output an error signal.

Figure 14:
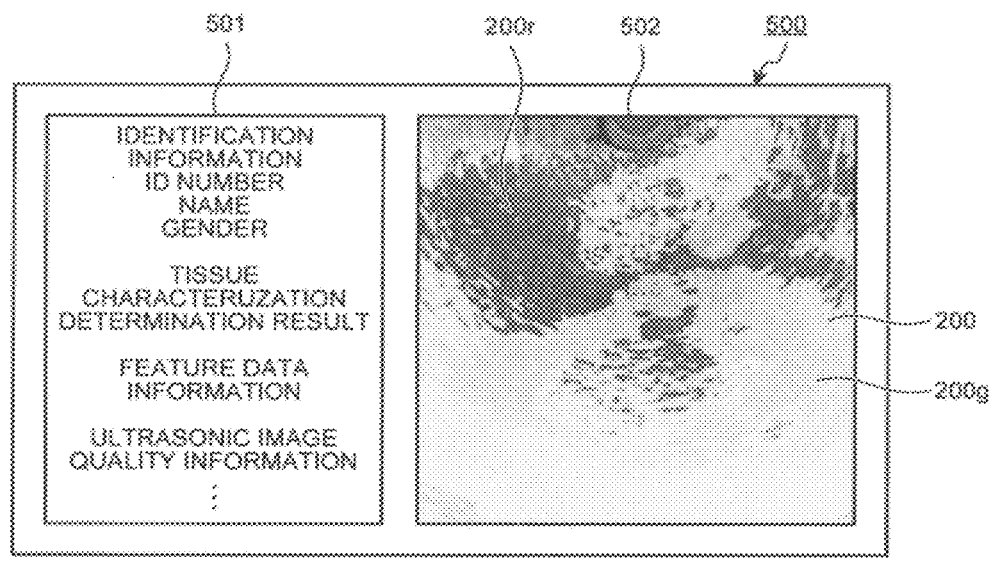
FIG. 14 is a diagram of a determination result display image that is displayed when the ultrasonic observation apparatus according to the first embodiment of the present invention determines tissue characterization based on the feature data.
Figure 15:
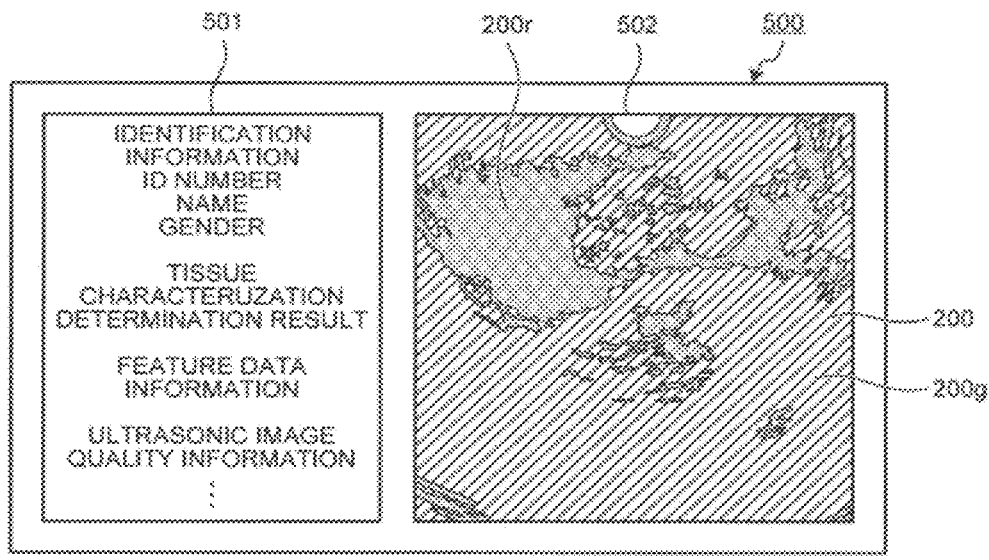
FIG. 15 is a diagram that schematically illustrates a black-and-white image of the image is illustrated in FIG. 14.

FIG. 14 is a diagram of a determination result display image that is displayed by the display unit 7 when the ultrasonic observation apparatus 1 determines the tissue characterization based on the feature data. FIG. 15 is a diagram that schematically illustrates a black-and-white image of the image is illustrated in FIG. 14. A determination result display image 500 illustrated in FIG. 14 and FIG. 15 includes an information displaying portion 501, which is used for displaying a variety of related information including the tissue characterization determination result, and an image displaying portion 502, which is used for displaying a feature data image. In FIG. 14 and FIG. 15, in the image displaying portion 502 is displayed the same feature data image 200 that is illustrated in FIG. 11 and FIG. 12.

In the information displaying portion 501, for example, following information is displayed: identification information (ID number, name, gender) of a specimen; the tissue characterization determination result; feature data information used in performing tissue characterization determination; and ultrasonic image quality information such as gain and contrast. Herein, as the feature data information, the display can be performed using the average and the standard deviation of feature data of the frequency spectrums of Q number of FFT data groups present inside the area of concern. More particularly, in the information displaying portion 501, for example, it is possible to display the following information: gradient=1.5±0.3 (dB/MHz); intercept=−60±2 (dB); and intensity=−50±1.5 (dB).

When the display unit 7 displays the determination result display image 500 having the abovementioned configuration, the operator can correctly understand the tissue characterization of the area of concern. However, determination result display images are not limited to the abovementioned configuration. Alternatively, for example, as a determination result display image, it is possible to display side-by-side a tissue characterization weighted image and a B-mode image. With that, the differences in the two images become recognizable on the same screen.

Second Embodiment

In a second embodiment of the present invention, the feature data extracting operation performed by a feature data extracting unit is different than the first embodiment. The configuration of an ultrasonic observation apparatus according to the second embodiment is same as the configuration of the ultrasonic observation apparatus 1 according to the first embodiment. Thus, in the following explanation, the constituent elements identical to those in the ultrasonic observation apparatus 1 are referred to by the same reference numerals.

During the feature data extracting operation according to the second embodiment, firstly, the attenuation correcting unit 422 performs attenuation correction with respect to the frequency spectrum calculated by the frequency analyzing unit 41. Then, the approximating unit 421 performs approximation with respect to the frequency spectrum that has been subjected to attenuation correction by the attenuation correcting unit 422, and extracts the feature data of the frequency spectrum.

Figure 16:
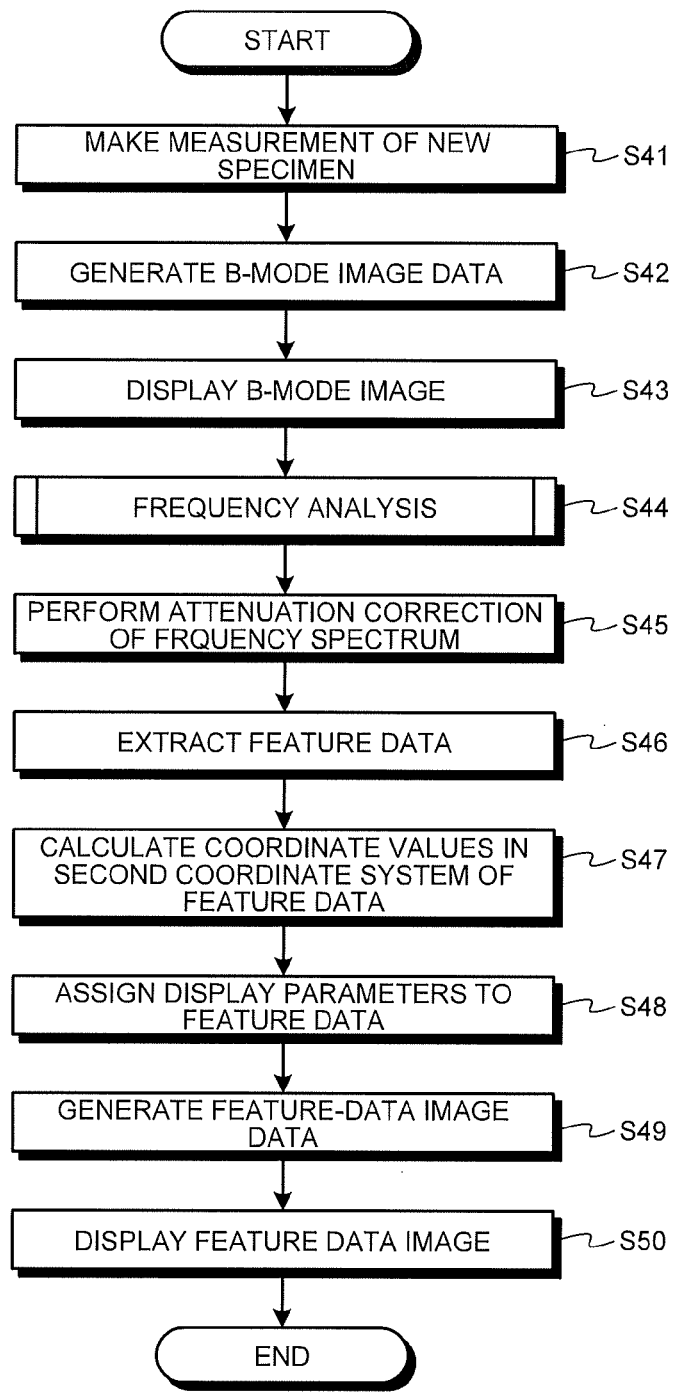
FIG. 16 is a flowchart explaining an overview of the operations performed by an ultrasonic observation apparatus according to a second embodiment of the present invention.

FIG. 16 is a flowchart explaining an overview of the operations performed by the ultrasonic observation apparatus according to the second embodiment. With reference to FIG. 16, the operations performed at Step S41 to S44 are respectively identical to the operations performed at Step S1 to S4 illustrated in FIG. 3.

Figure 17:
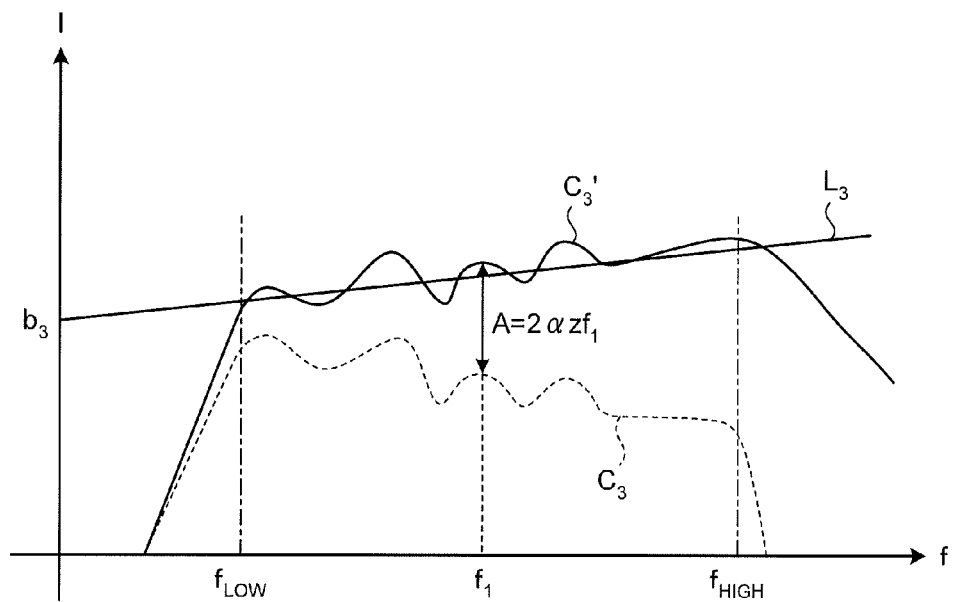
FIG. 17 is a diagram that schematically illustrates an overview of attenuation correction performed by the ultrasonic observation apparatus according to the second embodiment of the present invention.

At Step S45, the attenuation correcting unit 422 performs attenuation correction with respect to a frequency spectrum that is calculated by the frequency analyzing unit 41 by means of FFT (Step S45). FIG. 17 is a diagram that schematically illustrates an overview of the operation performed at Step S45. As illustrated in FIG. 17, with respect to a frequency spectrum curves $C_3$, the attenuation correcting unit 422 performs correction in the form of adding the attenuation amount A given in Equation (1) to the intensity I for all frequencies f, and obtains a new frequency spectrum curve $C_3'$. As a result, it becomes possible to obtain a frequency spectrum in which the contribution of attenuation occurring due to the propagation of ultrasonic sound waves is reduced.

Subsequently, the approximating unit 421 performs regression analysis of all frequency spectrums that are subjected to attenuation correction by the attenuation correcting unit 422, and extracts the feature data of the frequency spectrums (Step S46). More particularly, the approximating unit 421 performs regression analysis and calculates the gradient a, the intercept b, and the intensity c at the central frequency $f_{MID}$, which characterize the linear expression. A straight line $L_3$ illustrated in FIG. 17 is a regression line (intercept $b_3$) obtained by performing the feature data extracting operation on the frequency spectrum curve $C_3$ at Step S46.

The operations performed at Step S47 to Step S50 are respectively identical to the operations performed at Step S7 to Step S10 illustrated in FIG. 3.

As described above, according to the second embodiment of the present invention, in a feature data space including a first coordinate system that has at least some of a plurality of sets of feature data, each of which being extracted with respect to one of a plurality of known specimens, as coordinate components; when a plurality of representative points each representing one of a plurality of groups obtained by classification on the basis of the information regarding each of a plurality of known specimens is projected on a predetermined axis, a new coordinate axis having a large sum of distances between adjacent representative points along a predetermined direction in the first coordinate system is considered as one of the coordinate axes of a second coordinate system; and the coordinate values of the feature data of a specimen in that second coordinate system are calculated and display parameters corresponding to the calculated coordinate values are assigned. Hence, it becomes possible to make clear distinction between different groups. As a result, the specimen can be observed with more accuracy as well as the observation result can be enhanced in terms of reliability.

Moreover, according to the second embodiment, since the coordinate values of the feature data of the specimen in the second coordinate system are calculated, since display parameters corresponding to the coordinate values are assigned, and since feature-data image data having pixel values determined according to the assigned display parameters is generated and displayed; it becomes possible for the user to clearly recognize the differences in the groups in an image.

Furthermore, according to the second embodiment, since the feature data is extracted after performing attenuation correction with respect to the frequency spectrums, it becomes possible to eliminate the effect of attenuation that occurs during the propagation of ultrasonic sound waves. That makes it possible to perform observation with a higher degree of accuracy.

Thus far, although the invention is described with reference to the abovementioned embodiments, the appended claims are not to be thus limited to the first and second embodiments explained above.

For example, when there is a bias in the distribution of representative points in the feature data space, it is also possible to perform γ correction. FIG. 18 is a diagram that schematically illustrates an overview of γ correction performed by an ultrasonic observation apparatus according to another embodiment of the present invention. With reference to FIG. 18, a point $Sp_1$ is a specimen point; and points $\mu_1$, $v_1$, and $\rho_1$ are representative points of each group obtained by grouping a plurality of known specimens in the feature space. As illustrated in the upper diagram in FIG. 18, of the representative points $\mu_1$, $v_1$, and $\rho_1$ of each group, the distance between the representative point $\mu_1$ and the representative point $v_1$ in the h-axis direction is smaller than the distance between the representative point $v_1$ and the representative point $\rho_1$ in the h-axis direction. In that regard, as illustrated in FIG. 18, the ultrasonic observation apparatus performs γ correction on the points in the feature data space in such a way that the distribution in the area in which feature data h is small is dispersive in nature (positive γ correction). As a result, as illustrated in the lower diagram in FIG. 18, a point $Sp_1'$ becomes the specimen point, and the distance between a representative point $\mu'_1$ and a representative point $v'_1$ in the h-axis direction increases. On the other hand, the distance between the representative point $v'_1$ and a representative point $\rho'_1$ in the h-axis direction decreases. As a result, a distribution is obtained in which the three representative points are dispersed along the h-axis direction in a substantially uniform manner.

In this way, when the ultrasonic observation apparatus performs γ correction in an appropriate manner; then, even if there is a bias in the distribution of a plurality of groups in the feature data space, it becomes possible to make clear distinction between different groups.

Meanwhile, although the explanation is given for performing gamma correction on the feature data, it is also possible to perform γ correction in advance on the h-axis. Moreover, γ correction can be performed not only on the components in the h-axis direction but also on the components in the v-axis direction.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An ultrasonic observation apparatus that transmits ultrasonic sound waves to a specimen and receives ultrasonic sound waves reflected from the specimen, the ultrasonic observation apparatus comprising:
   a frequency analyzing unit that analyzes frequencies of the received ultrasonic sound waves and calculates a frequency spectrum;
   a feature data extracting unit that performs approximation with respect to the frequency spectrum calculated by the frequency analyzing unit and extracts a plurality of sets of feature data of the frequency spectrum; and
   a display parameter assigning unit that, in a feature data space including a first coordinate system that contains at least some of sets of feature data being respectively extracted for known specimens as its coordinate components, calculates coordinate values of the feature data of the specimen in a second coordinate system and assigns display parameters corresponding to the calculated coordinate values, the second coordinate system having a new coordinate axis as one of its coordinate axes, the new coordinate axis being an axis on which sum of distances between adjacent representative points is large, the representative points representing respective groups obtained by classifying the known specimens on the basis of information regarding each known specimen, the distances being obtained when the adjacent representative points, which are adjacent along a predetermined coordinate axis in the first coordinate system, are projected on a predetermined axis.

2. The ultrasonic observer apparatus according to claim 1, wherein the new coordinate axis is a coordinate axis on which the sum of distances between the adjacent representative points, which are adjacent along the predetermined coordinate axis of the first coordinate system, is the largest value.

3. The ultrasonic observation apparatus according to claim 1, further comprising:
   an image processing unit that generates feature-data image data which has pixel values determined according to the display parameters assigned by the display parameter assigning unit to the feature data of the specimen; and
   a display unit that is capable of displaying images corresponding to feature-data image data generated by the image processing unit.

4. The ultrasonic observation apparatus according to claim 1, wherein the display parameters are variables constituting a color space.

5. The ultrasonic observation apparatus according to claim 4, wherein the variables constituting the color space are either one of specific components of a primary color system, specific components of a complementary color system, hues, color intensity values, and luminosity values.

6. The ultrasonic observation apparatus according to claim 1, wherein
   the image processing unit generates feature-data image data further using second-type display parameters that are associated with the coordinate values of the feature data of the specimen in a second new coordinate axis orthogonal to the new coordinate axis and that determine the display form of images independent of the display parameters.

7. The ultrasonic observation apparatus according to claim 6, wherein the second display parameters are variables constituting a color space.

8. The ultrasonic observation apparatus according to claim 7, wherein the variables constituting the color space are either one of specific components of a primary color system, specific components of a complementary color system, hues, color intensity values, and luminosity values.

9. The ultrasonic observation apparatus according to claim 1, wherein a plurality of specimens, each having feature data belonging to same group, has mutually same tissue characterization.

10. The ultrasonic observation apparatus according to claim 1, wherein the feature data extracting unit includes
    an approximating unit that performs an approximation operation with respect to the frequency spectrum calculated by the frequency analyzing unit and extracts pre-correction feature data as feature data prior to performing attenuation correction by which there is a decrease in the contribution of attenuation, which occurs due to the reception depth and the frequency of ultrasonic sound waves being propagated, with respect to the frequency spectrum; and
    an attenuation correcting unit that performs the attenuation correction with respect to the pre-correction feature data extracted by the approximating unit, and extracts feature data of the frequency spectrum.

11. The ultrasonic observation apparatus according to claim 1, wherein the feature data extracting unit includes
    an attenuation correcting unit that performs the attenuation correction with respect to the frequency spectrum; and
    an approximating unit that performs the approximation operation with respect to the frequency spectrum corrected by the attenuation correcting unit and extracts feature data of the frequency spectrum.

12. The ultrasonic observation apparatus according to claim 10, wherein the feature data extracting unit performs polynomial approximation with respect to the frequency spectrum by means of regression analysis.

13. The ultrasonic observation apparatus according to claim 12, wherein the approximating unit performs linear approximation with respect to the frequency spectrum and extracts a plurality of sets of feature data that include at least two components from among a gradient of the linear expression, an intercept of the linear expression, and an intensity that is determined using the gradient, the intercept, and a specific frequency included in the frequency band of the frequency spectrum.

14. The ultrasonic observation apparatus according to claim 10, wherein, greater the reception depth of ultrasonic sound waves, greater is the extent of correction performed by the attenuation correcting unit.

15. An operation method of an ultrasonic observation apparatus that transmits ultrasonic sound waves to a specimen and receives ultrasonic sound waves reflected from the specimen, the operation method comprising:
    calculating that includes analyzing frequencies of the received ultrasonic sound waves and calculating a frequency spectrum by a frequency analyzing unit;
    extracting that includes performing approximation with respect to the frequency spectrum that has been calculated and extracting sets of feature data of the frequency spectrum by a feature data extracting unit; and
    assigning that includes calculating, in a feature data space including a first coordinate system that contains at least some of sets of feature data being respectively extracted for known specimens as its coordinate components, coordinate values of the feature data of the specimen in a second coordinate system and assigning display parameters corresponding to the calculated coordinate values by a display parameter assigning unit, the second coordinate system having a new coordinate axis as one of its coordinate axes, the new coordinate axis being an axis on which sum of distances between adjacent representative points is large, the representative points representing respective groups obtained by classifying the known specimens on the basis of information regarding each known specimen, the distances being obtained when the adjacent representative points, which are adjacent along a predetermined coordinate axis in the first coordinate system, are projected on a predetermined axis.

16. A non-transitory computer readable recording medium with an executable program stored thereon, wherein the program instructs a processor to perform:

calculating that includes analyzing frequencies of ultrasonic sound waves received from a specimen and calculating a frequency spectrum by a frequency analyzing unit;

extracting that includes performing approximation with respect to the frequency spectrum that has been calculated and extracting sets of feature data of the frequency spectrum by a feature data extracting unit; and assigning that includes calculating, in a feature data space including a first coordinate system that contains at least some of sets of feature data being respectively extracted for known specimens as its coordinate components, coordinate values of the feature data of the specimen in a second coordinate system and assigning display parameters corresponding to the calculated coordinate values by a display parameter assigning unit, the second coordinate system having a new coordinate axis as one of its coordinate axes, the new coordinate axis being an axis on which sum of distances between adjacent representative points is large, the representative points representing respective groups obtained by classifying the known specimens on the basis of information regarding each known specimen, the distances being obtained when the adjacent representative points, which are adjacent along a predetermined coordinate axis in the first coordinate system, are projected on a predetermined axis.

\* \* \* \* \*